United States Patent [19]

Morimoto et al.

[11] Patent Number: 5,120,721
[45] Date of Patent: Jun. 9, 1992

[54] ACARICIDAL COMPOSITION

[75] Inventors: Teruichi Morimoto, Shimada; Haruo Sasayama, Fuji; Kiyoshi Kasamatsu, Kobe, all of Japan

[73] Assignee: Sumitomo Chemical Company, Limited, Osaka, Japan

[21] Appl. No.: 589,598

[22] Filed: Sep. 28, 1990

[30] Foreign Application Priority Data

Oct. 6, 1989 [JP] Japan .................... 1-262710

[51] Int. Cl.$^5$ .................... A01N 57/02; A01N 57/10
[52] U.S. Cl. ............................ 514/103; 514/102; 514/108; 514/521; 514/523
[58] Field of Search ............... 514/103, 521, 523, 108

[56] References Cited

U.S. PATENT DOCUMENTS

| 2,873,228 | 2/1959 | Willard et al. | 514/103 |
| 3,835,176 | 9/1974 | Matsuo et al. | 558/407 |
| 4,260,633 | 4/1981 | Anderson et al. | 514/521 |
| 4,411,912 | 10/1983 | Henrick et al. | 514/521 |

FOREIGN PATENT DOCUMENTS

| 56-29509 | 3/1981 | Japan | 514/521 |
| 63-145206 | 6/1988 | Japan | 514/521 |
| 2113549 | 8/1983 | United Kingdom | 514/521 |

OTHER PUBLICATIONS

Farm Chemicals Handbook '87, pp. C115, 109, 119–120.
Webster's New International Dictionary of the English Language, 2nd edition, 1940, unabridged, p. 13.

Primary Examiner—Allen J. Robinson
Assistant Examiner—John D. Pak
Attorney, Agent, or Firm—Stevens, Davis, Miller & Mosher

[57] ABSTRACT

An acaricidal composition comprising as active ingredients
(A) either α-cyano-3-phenoxybenzyl 2,2,3,3-tetramethylcyclopropanecarboxylate or α-cyano-3-phenoxybenzyl N-(2-chloro-α,α,α-trifluoro-p-tolyl)-valinate, and
(B) O,O,O',O'-tetraethyl S,S'-methylene bis(phosphorodithioate), is very effectively applicable as a composition for controlling acarine pests such as two-spotted spider mite (*Tetranychus urticae* Koch), carmine spider mite (*Tetranychus cinnabarinus* Boisduval), Kanazawa spider mite (*Tetranychus Kansawai* Kishida), citrus red mite (*Panonychus citri* McGregor), European red mite (*Panonychus ulmi* Koch), broad mite (*Polyphagotarsonemus latus* Banks), etc. in areas cultivated with fruit trees, tea-plant, vegetables, flowering plants, etc.

5 Claims, No Drawings

ACARICIDAL COMPOSITION

The present invention relates to a novel acaricidal composition which permits effective control of acarine pests such as spider mites (Tetranychidae), eriophyid mites (Eriophydae), tarsonemid mites (Tarsonemidae), etc.

Some organophosphorus insecticides have an acaricidal activity. However, few of them are now sufficiently effective as acaricides since there have spread spider mites resistant to organophosphorus compounds. Synthetic pyrethroid compounds, even a group of synthetic pyrethroid compounds of highest acaricidal activity, do not have a sufficient controlling effect on spider mites.

For remedying such defects, there are already known acaricidal compositions obtained by mixing an organophosphorus insecticide with a synthetic pyrethroid compound. For example, there can be named a composition obtained by mixing fenpropathrin with acephate (JP-A-63-145206), a composition obtained by mixing fenpropathrin with dimethoate and the like (JP-A-56-29509), and a composition obtained by mixing ethion with cypermethrin and the like (JP-A-58-128309). These compositions, however, are not always sufficient in efficacy and the like.

Other than these, agents exclusively for controlling acarine pests, such as dicofol, fenbutatin oxide and hexythiazox are also known. However, in recent years, the effect of these agents has also been lessened. Therefore, it has been desired to develop a novel acaricide.

Employment of various acaricides over a long term of years results in appearance of acarine pests highly resistant to these acaricides in various parts of the world. Of these acarine pests, acarine pests having a particularly developed agent-resistance are two-spotted spider mite (*Tetranychus urticae* Koch), carmine spider mite (*Tetranychus cinnabarinus* Boisduval), Kanzawa spider mite (*Tetranychus kanzawai* Kaishida), citrus red mite (*Panonychus citri* McGregor), European red mite (*Panonychus ulmi* Koch), broad mite (*Polyphagotarsonemus latus* Banks) and the like. They are parasitic on fruit trees, vegetables, tea-plant, flowering plants, etc. Therefore, many acaricides are losing their utility against these acarine pests.

Accordingly, it has been eagerly desired to develop a novel acaricide which is markedly effective also against acarine pests having a developed resistance due to employment of conventional acaricides, even when applied at a small dosage, and which has only a low toxicity and slight undesirable influence on the environment.

It is an object of the present invention to provide a novel acaricide satisfying such requirements.

According to the present invention, there are provided an acaricidal composition (hereinafter the present composition) comprising as active ingredients (A) either α-cyano-3-phenoxybenzyl 2,2,3,3-tetramethylcyclopropanecarboxylate (hereinafter fenpropathrin) or α-cyano-3-phenoxybenzyl N-(2-chloro-α,α,α-trifluoro-p-tolyl valinate (hereinafter fluvalinate), and (B) O',O'-tetraethyl S,S'-methylene bis(phosphorodithioate) (hereinafter ethion); a process for producing an acaricide such as wettable powder, emulsifiable concentrate or the like which comprises said acaricidal composition; and a method for controlling acarine pests using said acaricide.

By virtue of combined use of either fenpropathrin or fluvalinate and ethion, the present composition has an excellent acaricidal activity on acarine pests such as two-spotted spider mite (*Tetranychus urticae* Koch), carmine spider mite (*Tetranychus cinnabarinus* Boisduval), Kanzawa spider mite (*Tetranychus kanzawai* Kishida), citrus red mite (*Panonychus citri* McGregor), European red mite (*Panonychus ulmi* Koch), broad mite (*Polyphagoarsonemus latus* Banks), etc. on fruit trees, vegetables, tea-plant, flowering plants and the like. This beneficial property cannot be obtained by independently using each of the above active ingredients. In detail, the present composition has the following desirable properties:

1. The composition shows an unexpectedly high synergistic effect in controlling acarine pests such as two-spotted spider mite (*Tetranychus urticae* Koch), citrus red mite (*Panonychus citri* McGregor), Kanzawa spider mite (*Tetranychus kanzawai* Kishida), etc., which are parasitic on agricultural and horticultural crops, as compared with the case where each of the active ingredients is used alone. Moreover, the synergistically effective acaricidal activity is immediate and is maintained at high level for a long period. Consequently, these acarine pests can be immediately controlled and prevented for a long period of time by virtue of the combined use of the active ingredients whereas the mere use of each active ingredient alone is not effective at all.

2. The composition has a marked acaricidal effect also on acarine pests having a developed resistance to various organic synthetic acaricides.

3. The composition has no significant phytotoxicity to agricultural and horticultural crops.

4. The composition is clearly superior in acaricidal activity to a composition obtained by mixing fenpropathrin with acephate (JP-A-63-145206), a composition obtained by mixing fenpropathrin with dimethoate and the like (JP-A-56-29509) and a composition obtained by mixing ethion with cypermethrin and the like (JP-A-58-128309) on which compositions have already been sought patent protections.

The present composition acts particularly on adults, young and larvae of acarine pests immediately and is excellent in durability of its effect. Furthermore, the inherent insecticidal activity of each active ingredient against other insect pests is kept high and not deteriorated at all by the combined use.

A formulation method and an application method of the present composition are specifically explained below.

For producing the present composition, it is sufficient that the active ingredients according to the present invention are blended with one or more suitable carriers and one or more suitable adjuvants such as surface active agents, binders, stabilizers and the like, and formulating the mixture into a wettable powder, emulsifiable concentrate, flowable, dust, DL (driftless-type) dust, or the like.

In this case, the mixing ratio of either fenpropathrin or fluvalinate to ethion is 1:1 to 1:100, preferably 1:1 to 1:50, more preferably 1:1 to 1:10. The total content of the active ingredients in the formulation is 1 to 80% by weight, preferably 20 to 40% by weight.

The carriers usable in the present composition are not critical and either solid or liquid carriers may be used so long as they are conventionally used in agricultural or horticultural agents.

The solid carriers include, for example, mineral powders, vegetable powders, alumina, silicates, sugar polymers and waxes.

The liquid carriers include, for example, water, alcohols, aromatic hydrocarbons, halogenated hydrocarbons, ethers, ketones, esters, nitriles, alcohol ethers, aliphatic or alicyclic hydrocarbons, industrial gasoline, and petroleum cut.

In the formulation into an emulsifiable concentrate, wettable powder, flowable, or the like, surface active agents, emulsifiers, etc. are used for the purpose of emulsification, dispersion, solubilization, wetting, foaming, lubrication, spreading, etc. In addition, a suitable amount of stabilizers such as antioxidants, ultraviolet absorbers and the like can be added if necessary.

The present composition can be used in admixture with other acaricides, insecticides, attractants, repellents, fungicides, plant growth regulators, fertilizers, etc. Such combined use permits extension of the range of application (blight and noxious insects to which the composition can be applied, application method, the timing of application, etc.).

A method for applying the present composition is as follows. Although varied depending on the size of a crop, the amount used of the composition is generally such that the total amount of the active ingredients, i.e., either fenpropathrin or fluvalinate and ethion is 0.3 to 550 g, preferably 2 to 150 g, per 10 ares. For applying the composition in the form of a wettable powder or an emulsifiable concentrate, the wettable powder or the emulsifiable concentrate is diluted with water and applied to a crop usually in a volume of 30 to 2,000 liters, preferably 50 to 500 liters, per 10 ares at a season at which acarine pests appear.

As compared with employment of each active ingredient alone, the present composition has an unexpectedly high synergistic effect in controlling acarine pests, for example, citrus red mite (*Panonychus citri* McGregor) and pink citrus rust mite (*Aculops pelekassi* Keifer) on citrus fruits; European red mite (*Panonychus ulmi* Koch), two-spotted spider mite (*Tetranychus urticae* Koch), hawthorn spider mite (*Tetranychus viennensis* Zacher), Kanzawa spider mite (*Tetranychus kanzawai* Kishida) and pear rust mite (*Epitrimerus pyri* Nalepa) on desiduous fruit trees; Kanzawa spider mite (*Tetranychus kanzawai* Kishida) on tea-plant; and two-spotted spider mite (*Tetranychus urticae* Koch), Kanzawa spider mite (*Tetranychus kanzawai* Kishida), carmine spider mite (*Tetranychus cinnabarinus* Boisduval) and broad mite (*Polyphagotarsonemus latus* Banks) on vegetables and flowering plants. The present composition permits very effective control of these acarine pests.

Table 1 shows the structural formulas of fenpropathrin, fluvalinate and ethion which are the active ingredients of the present composition.

TABLE 1

| Compound | Structural formula |
| --- | --- |
| Fenpropathrin | (structure with CH$_3$ groups, CHCOCH, CN, and phenyl-O-phenyl) |
| Fluvalinate | CF$_3$—(Cl-phenyl)—NHCHCOCH(=O)—O—(phenyl)—(phenyl); CH(CH$_3$)$_2$; CN |
| Ethion | (C$_2$H$_5$O)$_2$PSCH$_2$SP(OC$_2$H$_5$)$_2$ with S=P groups |

Of these compounds, fenpropathrin and fluvalinate have stereoisomers. Of the stereoisomers, each of the isomers and the mixtures thereof are included in the present invention.

Some examples are described below but the blending proportions of active ingredients, the kinds and amounts of adjuvants, etc. are not limited to those described in the examples. In the examples, parts are all by weight.

FORMULATION EXAMPLE 1

A wettable powder is obtained by uniformly mixing and pulverizing 10 parts of either fenpropathrin or fluvalinate, 30 parts of ethion, 5 parts of sodium lauryl sulfate, 2 parts of condensation product between sodium naphthalenesulfonate and formaldehyde, 20 parts of white carbon and 33 parts of clay.

FORMULATION EXAMPLE 2

An emulsifiable concentrate is obtained by mixing and dissolving 10 parts of either fenpropathrin or fluvalinate, 10 parts of ethion, 15 parts of Sorpol ® 2564 (a nonionic-anionic mixed emulsifier, mfd. by Toho Chemical Co., Ltd.) and 65 parts of xylol.

FORMULATION EXAMPLE 3

An emulsifiable concentrate is obtained by mixing and dissolving 5 parts of either fenpropathrin or fluvalinate, 35 parts of ethion, 15 parts of Sorpol ® 2564 (a nonionic-anionic mixed emulsifier, mfd. by Toho Chemical Co., Ltd.) and 45 parts of xylol.

FORMULATION EXAMPLE 4

A wettable powder is obtained by uniformly mixing and pulverizing 5 parts of either fenpropathrin or fluvalinate, 30 parts of ethion, 5 parts of sodium lauryl sulfate, 2 parts of condensation product between sodium naphthalenesulfonate and formaldehyde, 20 parts of white carbon and 38 parts of clay.

Next, the advantageous effect and utility of the present composition are illustrated with the following test examples.

TEXT EXAMPLE 1

There was investigated, by a laboratory test, acaricidal activity against female adult citrus red mites (*Panonychus citri* McGregor) which were resistant to organophosphorus compounds, organotin compounds and hexythiazox and were in course of rearing for successive generations on Chinese citron seedlings planted in a glass greenhouse. The female adult citrus red mites were inoculated on Chinese citron leaves fixed on an agar gel, allowed to oviposit for 24 hours. Then, they were sprayed with each of aqueous dilutions having a predetermined concentration of each of the emulsifiable concentrates of the present composition prepared in accordance with Formulation Examples 2 and Formulation Example 3, in a volume of 30 liters per 10 ares with a metering sprayer. The adult-killing effect was investigated after 2 days and the egg-killing effect after 10 days. The test was carried out with duplicate groups of 10 adults each, for each aqueous dilution. Table 2 shows the results. In Test Examples, 1 and 2, the term "egg-killing effect" means the sum of killing effects on eggs and hatched larvae.

TABLE 2

| Preparation tested | Concentration of aqueous spray (active ingredient ppm) | Adult-killing rate (%) | Egg-killing rate (%) |
| --- | --- | --- | --- |
| Fenpropathrin + ethion (emulsifiable concentrate) | 20 + 20<br>10 + 10<br>5 + 5 | 100<br>100<br>90 | 100<br>96<br>65 |
| Fenpropathrin + ethion (emulsifiable concentrate) | 20 + 140<br>10 + 70<br>5 + 35 | 100<br>100<br>90 | 100<br>100<br>98 |
| Fluvalinate + ethion (emulsifiable concentrate) | 20 + 140<br>10 + 70<br>5 + 35 | 100<br>100<br>65 | 100<br>100<br>80 |
| Fenpropathrin + dimethoate (emulsifiable concentrate) | 20 + 140<br>10 + 70 | 100<br>90 | 89<br>68 |
| Fenpropathrin (emulsifiable concentrate) | 20<br>10<br>5 | 55<br>45<br>35 | 59<br>45<br>12 |
| Fluvalinate (emulsifiable concentrate) | 20<br>10 | 25<br>5 | 62<br>15 |
| Ethion (emulsifiable concentrate) | 200<br>100 | 35<br>0 | 19<br>7 |
| Dimethoate (emulsifiable concentrate) | 100 | 5 | 0 |
| Hexythiazox (wettable powder) | 40<br>20 | 0<br>0 | 11<br>5 |

Note:
(The hexythiazox wettable powder is an acaricide described in Japan Plant Epidemic Prevention Association (an incorporated body), "Mannual of Agricultural Chemicals 1986", p. 433-434 (Dec. 10, 1986).

TEXT EXAMPLE 2

There was investigated by a laboratory test, acaricidal activity against female adults and eggs of Kanzawa spider mite (*Tetranychus kanzawai* Kishida) which were resistant to organophosphorus compounds and organotin compounds and were in course of rearing for successive generations of kidney bean young seedlings in a room at a constant temperature of 25° C. The female adult Kanzawa spider mites were inoculated on kidney bean leaves fixed on an agar gel, allowed to oviposit for 24 hours. Then, they were sprayed with each of aqueous dilutions having predetermined concentrations of each synthetic pyrethroid formulation alone, each organophosphorus formulation alone or each of mixtures of a synthetic pyrethroid formulation and an organophosphorus formulation which included the combination of the present invention, in a volume of 30 liters per 10 ares with a metering sprayer. The adult-killing effect was investigated after 2 days and the egg-killing effect after 9 days. The test was carried out with duplicate groups of 10 adults each, for each aqueous dilution. Table 3 shows the results.

TABLE 3

| Preparation tested | Concentration of aqueous spray (active ingredient ppm) | Adult-killing rate (%) | Egg-killing rate (%) |
| --- | --- | --- | --- |
| Fenpropathrin (emulsifiable concentrate) + ethion (emulsifiable concentrate) | 10 + 100<br>5 + 50 | 100<br>100 | 100<br>100 |
| Fenpropathrin (emulsifiable concentrate) + acephate (wettable powder) | 10 + 100<br>5 + 50 | 89<br>56 | 34<br>19 |
| Cypermethrin (emulsifiable concentrate + ethion (emulsifiable concentrate) | 10 + 100<br>5 + 50 | 67<br>44 | 5<br>2 |
| Fenpropathrin (emulsifiable concentrate) | 10<br>5 | 56<br>22 | 22<br>8 |
| Cypermethrin (emulsifiable concentrate) | 10 | 11 | 2 |
| Ethion (emulsifiable concentrate) | 100 | 44 | 3 |
| Acephate (wettable powder) | 100 | 0 | 0 |
| Fenbutatin oxide (wettable powder) | 125 | 44 | 2 |

Note: The fenbutatin oxide wettable powder is an acaricide described in Japan Plant Epidemic Prevention Association (an incorporated body), "Handbook of Agricultural Chemicals 1985", p. 123 (Jan. 30, 1986).

TEST EXAMPLE 3

Twenty female adult two-spotted spider mites (*Tetranychus urticae* Koch) which were resistant to organophosphorus compounds and organotin compounds and were in course of rearing for successive generations, were inoculated on each kidney bean plate of the 5-6 leaf stage planted in a glass greenhouse, settled thereon, and allowed to oviposit. Seven days after the settlement and oviposition, each of aqueous dilutions having a predetermined concentration of the wettable powder of the present invention prepared in accordance with Formulation Example 1 was sprayed upon the kidney bean plants in a volume of 100 liters per 10 ares with a hand sprayer. Immediately before the spraying and 3 days, 10 days, 20 days and 30 days after the spraying, the number of female adult two-spotted spider mites parasitic on the plants and phytotoxicities were investigated, and the controlling degree (%) was calculated.

The test was carried out with triplicate groups of one plant each, for each aqueous dilution. Table 4 shows the results. The controlling degree (%) in the test example was calculated according to the following equation (hereinafter the same applied):

$$\text{Controlling degree (\%)} = \left(1 - \frac{T_b/T_a}{C_b/C_a}\right) \times 100$$

wherein $C_a$: the number of mites before the spraying in an untreated group $C_b$: the number of mites after the spraying in the untreated group $T_a$: the number of mites before the spraying in a treated group $T_b$: the number of mites after the spraying in the treated group

TABLE 4

| Preparation tested | Concentration of aqueous spray (active ingredient ppm) | Controlling degree (%) | | | | Phytotoxicity |
|---|---|---|---|---|---|---|
| | | After 3 days | After 10 days | After 20 days | After 30 days | |
| Fenpropathrin + ethion (wettable powder) | 50 + 150<br>25 + 75 | 100<br>100 | 100<br>100 | 98<br>95 | 91<br>83 | None<br>None |
| Fenpropathrin (wettable powder) | 50 | 90 | 50 | 20 | 0 | None |
| Ethion (wettable powder) | 500 | 13 | 0 | 0 | 0 | None |

TEST EXAMPLE 4

Each of aqueous dilutions having a predetermined concentration of the emulsifiable concentrate of the present invention prepared in accordance with Formulation Example 3 was sprayed upon tangerine (Okitsu wase Citrus unshu) trees planted in No. 10 unglazed pots and infested with a large number of citrus red mites (*Panonychus citri* McGregor), in a volume of 300 liters per 10 ares with a hand sprayer. Immediately before the spraying and 3 days, 10 days, 20 days and 30 days after the spraying, the number of female adult citrus red mites parasitic on 20 optional leaves of each tree an dphytotoxicities were investigated, and the controlling degree (%) was calculated.

The test was carried out with triplicate groups of one tree each, for each aqueous dilution. Table 5 shows the results.

TABLE 5

| Preparation tested | Concentration of aqueous spray (active ingredient ppm) | Controlling degree (%) | | | | Phytotoxicity |
|---|---|---|---|---|---|---|
| | | After 3 days | After 10 days | After 20 days | After 30 days | |
| Fenpropathrin + ethion (emulsifiable concentrate) | 50 + 350<br>25 + 175 | 100<br>100 | 98<br>98 | 94<br>90 | 93<br>88 | None<br>None |
| Fenpropathrin + dimethoate (emulsifiable concentrate) | 50 + 350 | 98 | 98 | 67 | 55 | None |
| Fenpropathrin (emulsifiable concentrate) | 50 | 95 | 89 | 46 | 0 | None |
| Ethion (emulsifiable concentrate) | 500 | 95 | 90 | 48 | 0 | None |
| Dimethoate (emulsifiable concentrate) | 350 | 0 | 0 | 0 | 0 | None |

TEXT EXAMPLE 5

Female adult two-spotted spider mites (*Tetranychus urticae* Koch) which were resistant to organophosphorus compounds and were in course of rearing for successive generations, were made parasitic on kidney bean plants planted in pots (diameter: 9 cm) in an artificial climate chamber. Each of aqueous dilutions having a predetermined concentration of the wettable powder of the present invention prepared in accordance with Formulation Example 4 was sprayed upon the kidney bean plants in a volume of 30 ml per 3 pots. The pots were then stored in a room at 25° C.±1° C. The female adult two-spotted spider mites was counted before the spraying and on predetermined days after the spraying. Table 6 shows the results.

TABLE 6

| Preparation tested | Concentration of aqueous spray (active ingredient ppm) | Number of female two-spotted spider mites per 3 pots | | | |
|---|---|---|---|---|---|
| | | Before spraying | After 3 days | After 10 days | After 20 days |
| Fenpropathrin + ethion (wettable powder) | 50 + 300 | 53 | 0 | 0 | 0 |
| Fluvalinate + ethion (wettable powder) | 50 + 300 | 45 | 0 | 2 | 10 |
| Fenpropathrin (wettable powder) | 50 | 60 | 8 | 12 | 33 |
| Fluvalinate (wettable powder) | 50 | 36 | 10 | 15 | 50 |

TABLE 6-continued

| Preparation tested | Concentration of aqueous spray (active ingredient ppm) | Number of female two-spotted spider mites per 3 pots | | | |
|---|---|---|---|---|---|
| | | Before spraying | After 3 days | After 10 days | After 20 days |
| Ethion (wettable powder) | 300 | 23 | 30 | 47 | 125 |
| Untreated | — | 30 | 35 | 59 | 128 |

The present composition is very effectively applicable as a composition for controlling acarine pests such as two-spotted spider mite (*Tetranychus urticae* Koch), carmine spider mite (*Tetranychus cinnabarinus* Boisduval), Kanzawa spider mite (*Tetranychus kanzawai* Kishida), citrus red mite (*Panonychus citri* McGregor), European red mite (*Panonychus ulmi* Koch), broad mite (*Polyphagotarsonemus latus* Banks), tec. in areas cultivated with fruit trees, tea-plant, vegetables, flowering plants, etc.

What is claimed is:

1. An acaricidal composition comprising as active ingredients a synergestically acaricidally effective amount of
   (A) either α-cyano-3-phenoxybenxyl 2,2,3,3-tetramethylcyclopropanecarboxylate or α-cyano-3-phenoxybenzyl N-(2-chloro-α,α,α-trifluoro-p-tolyl)valinate, and
   (B) O',O'-tetraethyl S,S'-methylene bis(phosphorodithioate) wherein the ratio of (A) to (B) ranges from 1:1 to 1:10.

2. The composition of claim 1, wherein the component (A) is α-cyano-3-phenoxybenxyl 2,2,3,3-tetrmethylcyclopropanecarboxylate.

3. A method for controlling acarine pests which comprises applying to plants a synergistically a caricidally effective amount of an acaricidal composition comprising as active ingredients
   (A) either α-cyano-3-phenoxybenzyl 2,2,3,3-tetramethylcyclopropanecarboxylate or α-cyano-3-phenoxybenxyl N-(2-chloro-α,α,α-trifluoro-p-tolyl)valinate, and
   (B) O,O,O',O',-tetraethyl S,S'-methylene bis(phosphorodithioate) wherein the ratio of (A) to (B) ranges from 1:1 to 1:10.

4. The composition of claim 1, wherein the total content of the active ingredients in the composition is from 1 to 80% by weight.

5. The composition of claim 2, wherein the total content of the active ingredients in the composition is from 1 to 80% by weight.

* * * * *